US005476845A

United States Patent [19]

[11] Patent Number: 5,476,845

[45] Date of Patent: Dec. 19, 1995

Reizlein et al.

[54] USE OF PHOSPHORIC ESTERS AS CRYSTALLIZATION INHIBITORS

[75] Inventors: Karl Reizlein, Cologne; Klaus Wangermann, Krefeld; Wolfgang Wirth, Bergisch Gladbach, all of Germany

[73] Assignee: Bayer Aktiengesellschaft, Leverkusen, Germany

[21] Appl. No.: 336,635

[22] Filed: Nov. 9, 1994

[30] Foreign Application Priority Data

| | | | |
|---|---|---|---|
| Nov. 16, 1993 | [DE] | Germany | 43 39 119.2 |
| Jul. 8, 1994 | [DE] | Germany | 44 24 065.1 |

[51] Int. Cl.$^6$ .......... A01N 43/50

[52] U.S. Cl. .......... 514/63; 514/383; 548/110; 548/267.4; 548/267.8; 548/268.2; 548/268.4; 548/268.8

[58] Field of Search .......... 516/63, 383; 548/110, 548/267.4, 267.8, 268.2, 268.4, 268.8

[56] References Cited

U.S. PATENT DOCUMENTS

| | | | |
|---|---|---|---|
| 2,926,096 | 2/1960 | Sakornbut | 106/15 |
| 5,206,225 | 4/1993 | Horstmann et al. | 514/63 |
| 5,240,952 | 8/1993 | Brandes et al. | 514/376 |

FOREIGN PATENT DOCUMENTS

| | | |
|---|---|---|
| 085922 | 8/1983 | European Pat. Off. . |
| 328217 | 8/1989 | European Pat. Off. . |
| 0328217 | 8/1989 | European Pat. Off. . |
| 391171 | 10/1990 | European Pat. Off. . |
| 0391168 | 10/1990 | European Pat. Off. . |
| 453922 | 10/1991 | European Pat. Off. . |
| 453899 | 10/1991 | European Pat. Off. . |
| 453915 | 10/1991 | European Pat. Off. . |
| 0579052 | 7/1993 | European Pat. Off. . |
| 3631558 | 3/1988 | Germany . |
| 4140928 | 6/1993 | Germany . |
| 9206596 | 4/1992 | WIPO . |

*Primary Examiner*—Richard L. Raymond
*Attorney, Agent, or Firm*—Sprung Horn Kramer & Woods

[57] ABSTRACT

A new process for preventing the crystallization of certain azole derivatives in the spray equipment upon spraying mixtures containing A) certain azole derivatives which have a tendency to crystallize and B) if appropriate one or more other active compounds and additives, which process comprises adding at least one phosphoric ester of the formula

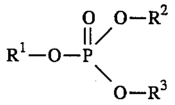

in which $R^1$ represents alkyl having 2 to 18 carbon atoms and $R^2$ and $R^3$ independently of one another represent alkyl having 2 to 12 carbon atoms, to the spray mixture before spraying.

7 Claims, No Drawings

USE OF PHOSPHORIC ESTERS AS CRYSTALLIZATION INHIBITORS

The present invention relates to the new use of certain phosphoric esters for preventing crystallization when aqueous spray mixtures based on certain fungicidal active compounds are applied.

The spray equipment which is conventionally used for applying aqueous formulations of plant-treatment products accommodates a plurality of filters and nozzles. For example, there are vacuum filters between the tank and the tank pump, and furthermore pressure filters, which are arranged downstream of the pump in the pressure section. Moreover, there may be nozzle filters arranged directly before the spray nozzles. All these filters and the nozzles can get clogged up more or less regularly by active compounds which crystallize out when aqueous spray mixtures based on solid active compounds are applied.

It has already been disclosed that the azole derivatives mentioned below are fungicidally active and can be applied to plants and/or their environment in the form of aqueous spray mixtures:

1-(4-chlorophenyl)-4,4-dimethyl-3-(1,2,4-triazol-1-yl-methyl)-pentan- 3-ol,
1-(4-chlorophenoxy)-3,3-dimethyl-1-(1,2,4-triazol-1-yl)-butan- 2-one,
1-(4-chlorophenoxy)-3,3-dimethyl-1-(1,2,4-triazol-1-yl)-butan- 2-ol,
1-(4-phenyl-phenoxy)-3,3-dimethyl-1-(1,2,4-triazol-1-yl)-butan- 2-ol,
1-( 4-fluorophenyl)-1-(2-fluorophenyl)-2-( 1,2,4-triazol-1-yl)-ethan-1-ol,
1-(1,2,4-triazol-1-yl)-2-(2,4-dichorophenyl)-hexan-2 -ol,
1-([bis-(4-fluorophenyl)-methyl-silyl]-methyl)-1H-(1,2,4-triazole),
1-(4-chlorophenyl)-2-(1,2,4-triazol-1-yl)-4,4-dimethyl-pent- 1-en-3-ol,
1-(2,4-dichlorophenyl)-2-(1,2,4-triazol-1-yl)-4,4-dimethyl-pent - 1-en-3-ol,
1-(4-chlorophenyl)-1-(1-cyclopropyl-ethyl)-2-(1,2,4-triazol- 1-yl )-ethan-1-ol,
1-( 4-chlorophenyl)-3-phenyl-3-cyano-4-(1,2,4-triazol-1-yl)-butane and
1-[3-(2-chlorophenyl)-2-(4-fluorophenyl)-oxiran-2-yl-methyl]- 1H-(1,2,4-triazole)

(Cf. EP-OS (European Published Specification) 0 040 345, DE-PS (German Patent Specification) 2 201 063, DE-PS (German Patent Specification) 2 324 010, EP-OS (European Published Specification) 0 015 756, US-PS (US Patent Specification) 4 551 469, EP-OS (European Published Specification) 0 068 813, DE-OS (German Published Specification) 2 838 847, DE-OS (German Published Specification) 3 010 560, DE-OS (German Published Specification) 3 406 993, DE-OS (German Published Specification) 2 821 971 and EP-OS (European Published Specification) 0 196 038.

Furthermore, it has been disclosed that N-alkyllactams and N,N-dimethylalkylcarboxamides can be used as crystallization inhibitors in the preparation and application of spray mixtures of the above-mentioned active compounds (cf. European Published Specifications 0 391 168 and 0 453 899). For example, N-octylpyrrolidone and/or a mixture with an average composition of 5% of N,N-dimethylhexanamide, 50% of N,N-dimethyloctanamide, 40% of N,N-dimethyldecanamide and 5% of N,N-dimethyldodecanamide, so as to prevent crystallization of the active compound in the spray equipment when aqueous spray mixtures which contain 1-(4-chlorophenyl)-4,4-dimethyl-3-(1,2,4-triazol-1-yl-methyl)-pentan- 3-ol as active compound are applied. However, the activity of the above-mentioned crystallization inhibitors is not always satisfactory when such spray mixtures are applied over a prolonged period.

Finally, it has also been disclosed that tributyl phosphate can be used to inhibit the crystallization of (±)-2-ethoxy-2,3-dihydro-3,3-dimethylbenzofuran-5-yl-methylsulphonate (=ethofumesate) in formulations of this herbicidal active compound (cf. European Published Specification 0 328 217). However, an analogous use in preparations of other agrochemical active compounds has not been described as yet.

It has now been found that phosphoric esters of the formula

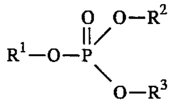

(I)

in which $R^1$ represents alkyl having 2 to 18 carbon atoms and $R^2$ and $R^3$ independently of one another represent alkyl having 2 to 12 carbon atoms, can be used when applying aqueous spray mixtures which contain A) at least one azole derivative of the formula

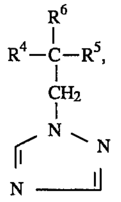

(II)

in which a) $R^4$ represents

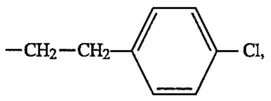

$R^5$ represents tert-butyl and $R^6$ represents hydroxyl, or b) $R^4$ represents 4-fluorophenyl, $R^5$ represents 2-fluorophenyl and $R^6$ represents hydroxyl, or c) $R^4$ represents 2,4-dichlorophenyl, $R^5$ represents n-butyl and $R^6$ represents hydroxyl, or

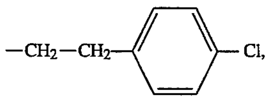

d) $R^4$ represents $R^5$ represents phenyl and $R^6$ represents cyano, or e) $R^4$ represents 4-chlorophenyl, $R^5$ represents

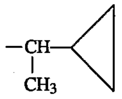

and $R^6$ represents hydroxyl, and/or at least one azole derivative of the formula (III)

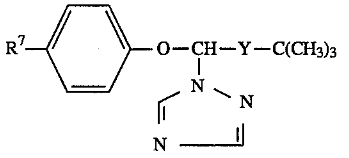

in which a) Y represents —CH(OH) and $R^7$ represents chlorine or phenyl, or b) Y represents CO and $R^7$ represents chlorine, and/or at least one azole derivative of the formula (IV)

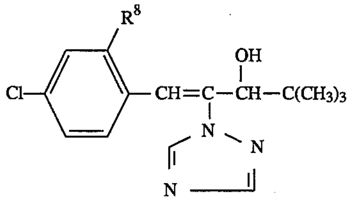

in which $R^5$ represents hydrogen or chlorine, and/or 1-([bis-(4-fluorophenyl)-methyl-silyl]-methyl)-1H-(1,2,4-triazole) of the formula (V)

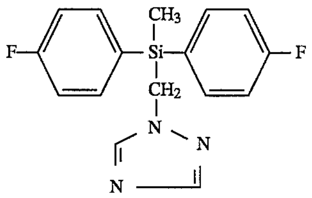

and/or

1-[3-(2-chlorophenyl)-2-(4-fluorophenyl)-oxiran-2-yl-methyl]-1H-(1,2,4-triazole) of the formula (VI)

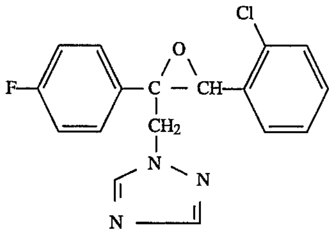

and

B) if appropriate one or more other active compounds and additives to prevent crystallization of the active compounds of the formulae (II) to (VI) in the spray equipment.

It is to be regarded as highly surprising that the tendency of azole derivatives of the formulae (II) to (VI) to crystallize is greatly reduced by the use according to the invention of phosphoric esters of the formula (I). Especially, it could not have been expected that phosphoric esters of the formula (I) are much better suited for the purpose indicated than N-alkyllactams and N,N-dimethylalkylcarboxamides.

The use of phosphoric esters of the formula (I) in aqueous formulations based on fungicidally active azole derivatives of the formulae (II) to (VI) has a series of advantages. For example, the phosphoric esters of the formula (I) are substances whose handling is problem-free and which are also available in substantial amounts. Furthermore, the use of the substances of the formula (I) prevents clogging of the filters and of the nozzles of the spray equipment when aqueous formulations containing active compounds of the formulae (II) to (VI) are applied by spraying. Another advantage is that phosphoric esters of the formula (I) have no unwanted side effects whatsoever in plant protection.

Formula (I) provides a general definition of the phosphoric esters which can be used according to the invention.

$R^1$ preferably represents straight-chain or branched alkyl having 4 to 12 carbon atoms.

$R^2$ preferably represents straight-chain or branched alkyl having 2 to 8 carbon atoms.

$R^3$ preferably represents straight-chain or branched alkyl having 2 to 8 carbon atoms.

$R^1$ particularly preferably represents n-butyl, iso-butyl, sec-butyl, tert-butyl, n-pentyl, n-hexyl, 2-ethyl-hexyl, n-heptyl, n-octyl, iso-octyl, n-nonyl, iso-nonyl, n-decyl, n-dodecyl or iso-dodecyl.

$R^2$ particularly preferably represents n-butyl, iso-butyl, sec-butyl, tert-butyl, n-pentyl, n-hexyl, 2-ethyl-hexyl, n-heptyl, n-octyl or iso-octyl.

$R^3$ particularly preferably represents n-butyl, iso-butyl, sec-butyl, tert -butyl, n-pentyl, n-hexyl, 2-ethyl-hexyl, n-heptyl, n-octyl or iso-octyl.

The following may be mentioned as examples of phosphoric esters which can be used according to the invention:

tri-n-butyl phosphate, tri-n-pentyl phosphate, tri-n-hexyl phosphate, tri-n-heptyl phosphate, tri-n-octyl phosphate, tri-(2-ethyl-hexyl)phosphate The phosphoric esters of the formula (I) are already known (see textbooks of Organic Chemistry).

Formulae (II) to (VI) provide a definition of the azole derivatives contained in the aqueous spray mixtures which can be used according to the invention. A single or alternatively several of the following azole derivatives can be contained.

1-(4-Chlorophenyl )-4,4-dimethyl-3-(1,2,4-triazol-1-yl-methyl)-pentan- 3-ol of the formula (II-a)

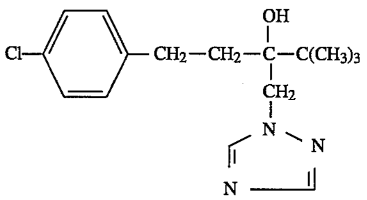

1-(4-Fluorophenyl-1-(2-fluorophenyl)-2-(1,2,4-triazol-1-yl)-ethan-1-ol of the formula (II-b)

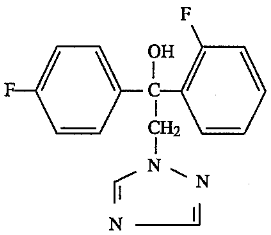

1-(1,2,4-Triazol-1-yl)-2-(2,4-dichlorophenyl)-hexan-2 -ol of the formula (II-c)

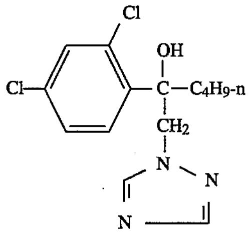

1-(4-Chlorophenyl)-3-phenyl-3-cyano-4-(1,2,4-triazol-1-yl)-butane of the formula (II-d)

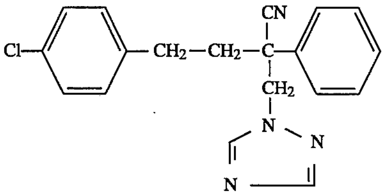

1-(4-Chlorophenyl)-1-(1-cyclopropyl-ethyl)-2-(1,2,4-triazol- 1-yl)-ethan-1-ol of the formula (II-e)

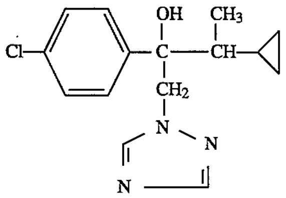

1-(4-Chlorophenoxy)-3,3-dimethyl-1-(1,2,4-triazol -1-yl)-butan- 2-ol of the formula (III-a)

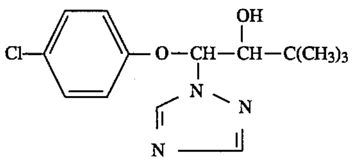

1-(4-Phenyl-phenoxy)-3,3-dimethyl-1-(1,2,4-triazol-1-yl)-butan- 2-ol of the formula (III-b)

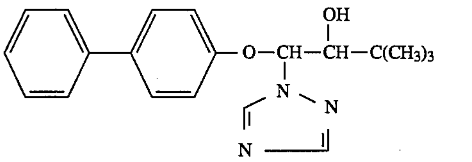

1-(4-Chlorophenoxy)-3,3-dimethyl-1-(1,2,4-triazol-1-yl)-butan- 2-one of the formula (III-c)

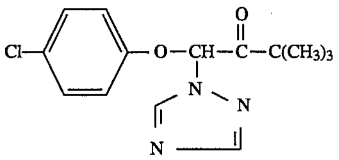

1-(4-Chlorophenyl )-2-(1,2,4-triazol-1-yl)-4,4-dimethyl-pent- 1-en-3-ol of the formula (IV-a)

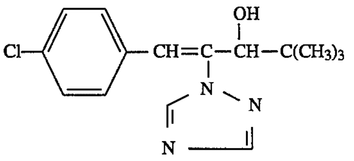

1-(2,4-Dichlorophenyl)-2-(1,2,4-triazol-1-yl)-4,4-dimethyl-pent-1-en-3-ol of the formula (IV-b)

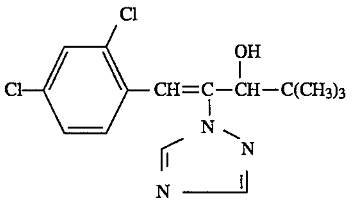

1-([Bis-(4-fluorophenyl)-methyl-silyl]-methyl)-1H-( 1,2, 4-triazole) of the formula (V)

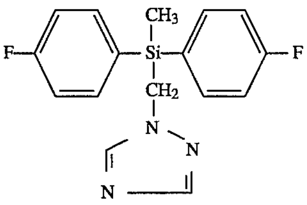

1-[3-(2-Chlorophenyl)-2-(4-fluorophenyl)-oxiran-2-yl-methyl]-1H-( 1,2,4-triazole) of the formula

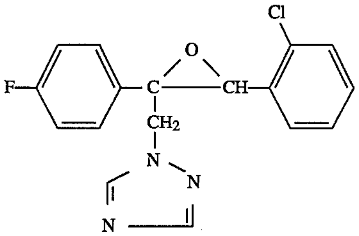

(VI)

The active compounds of the formulae (II) to (VI) and their use for combating phytopathogenic fungi have been disclosed (cf. EP-OS (European Published Specification) 0 040 345, US-PS (U.S. Pat. No. ) 4,551,469, EP-PS (European Published Specification) 0 015 756, EP-OS (European Published Specification) 0 068 813, DE-OS (German Published Specification) 3 406 993, DE-PS (German Patent Specification) 2 324 010, DE-PS (German Patent Specification) 2 201 063, DE-OS (German Published Specification) 2 838 847, DE-OS (German Published Specification) 3 010 560, DE-OS (German Published Specification) 2 821 971 and EP-OS (European Published Specification) 0 196 038.

The active compounds of the formulae (II) to (VI) can be used in the customary formulations. They are preferably applied in the form of aqueous spray mixtures.

The spray mixtures which can be used according to the invention can also contain one or more other active compounds in addition to the active compounds of the formulae (II) to (VI). Preferably suitable in this context are compounds which have fungicidal properties. The following may be mentioned as examples of such active compounds which can additionally be used:

N,N-dimethyl-N'-phenyl-(N'-fluorodichloromethylthio)sulphamide (dichlofluanid),
N,N-dimethyl-(N'-fluorodichloromethylthio)-N'-(4-methylphenyl)-sulphamide (tolylfluanid),
N-trichloromethylmercapto-4-cyclohexene-1,2-dicarboxamide (captan),
N-(1,1,2,2-tetrachloroethyl-sulphenyl)-cis-4-cyclohexene-1,2-dicarboxamide (captafol),
N-trichloromethylthio-phthalimide (folpet),
N-dodecyl-guanidine-acetate (dodine),
tetrachloro-isophthalo-dinitrile (chlorothalonile),
4,5,6,7-tetrachlorophthalide,
zinc ethylene-bis-dithiocarbamate (zineb),
manganese ethylene-bis-dithiocarbamate (maneb),
zinc ethylene-bis-dithiocarbamate/manganese-ethylene-bis-dithiocarbamate (mancozeb),
zinc propylene-1,2-bis-dithiocarbamate (propineb),
1-[3-(4-(1,1-dimethylethyl)-phenyl)-2-methylpropyl]-piperidine (fenpropidine),
N-tridecyl-2,6-dimethyl-morpholine (tridemorph),
N-dodecyl-2,6-dimethyl-morpholine (aldimorph) cis-4-[3-(4-tert-butylphenyl)-2-methyl-propyl]-2,6-dimethylmorpholine (fenpropimorph)
2-[2-(2,4-dichlorophenyl)-2-(2-propenyloxy)-ethyl]-imidazole (imazalil),
N-[2-(2,4,6-trichlorophenoxy)-ethyl]-N-propyl-1H-imidazole (prochloraz),
1-[2-(2,4-dichlorophenyl)-4-propyl-(1,3-dioxolan-2-yl) -methyl]-1H-(1,2,4-triazole) (propiconazole)
N-(3,5-dichlorophenyl)-1,2-dimethyl-cyclopropane-1,2 -dicarboximide (procymidone),
2-methoxycarbamoyl-benzimidazole (carbendazim),
1-(butylcarbamoyl)-2-benzimidazole-methylcarbamate (benomyl),
2,4-dichloro-6-(2'-chlorophenyl-amino)-1,3,4-triazine (anilazine),
bis-(8-guanidine-O-octyl)-amine-triacetate (guazatine),
1-(4-chlorobenzyl)-1-cyclopentyl-3-phenyl-urea (pencycuron).

Suitable additives which may be present in the spray mixtures which can be used according to the invention are surface-active substances, organic diluents, acids, low-temperature stabilizers and adhesives as well as other crystallization inhibitors.

Suitable surface-active substances are non-ionic, anionic, cationic and zwitterionic emulsifiers. These substances include reaction products of fatty acids, fatty acid esters, fatty alcohols, fatty amines, alkylphenols or alkylarylphenols with ethylene oxide and/or propylene oxide, and their sulphuric esters, phosphoric mono-esters and phosphoric di-esters, furthermore reaction products of ethylene oxide with propylene oxide, moreover alkylsulphonates, alkyl sulphates, aryl sulphates, tetra-alkyl-ammonium halides, tri-alkyl-aryl-ammonium halides and alkylamine sulphonates. The emulsifiers can be employed singly or else in the form of a mixture. The following may preferably be mentioned: reaction products of castor oil with ethylene oxide in a molar ratio of 1:20 to 1:60, reaction products of $C_6$–$C_{20}$ fatty alcohols with ethylene oxide in a molar ratio of 1:5 to 1:50, reaction products of fatty amines with ethylene oxide in a molar ratio of 1:2 to 1:20, reaction products of 1 mol of phenol with 2 to 3 of styrol and 10 to 50 of ethylene oxide, reaction products of 1 mol of phenol with 2 to 3 of vinyltoluene and 10 to 50 mols of ethylene oxide, reaction products of $C_8$–$C_{12}$ alkylphenols with ethylene oxide in a molar ratio of 1:5 to 1:30, alkyl glycosides, and salts of $C_8$–$C_{16}$ alkyl-benzenesulphonic acids, such as, for example, calcium, monoethanolammonium, di-ethanolammonium and triethanolammonium salts.

The emulsifiers from the group of the alkylaryl-poly-glycol-ethers which are used in practice are frequently mixtures of more than one compound. In particular, they are mixtures of substances which differ by the degree of substitution on the phenyl ring linked to the oxyethylene unit and by the number of oxyethylene units. This is why the averages which are calculated for the number of substituents on the phenyl ring include fractional numbers. Examples which may be mentioned are substances which have the following average compositions:

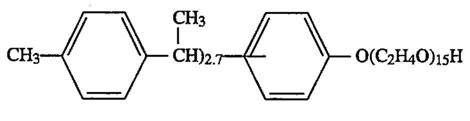

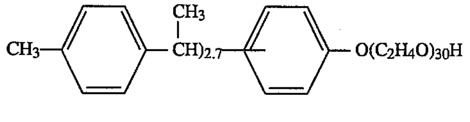

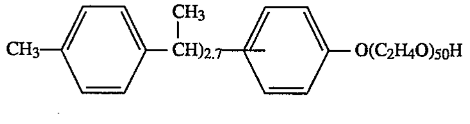

-continued

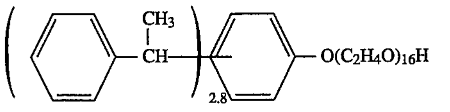

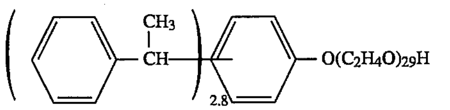

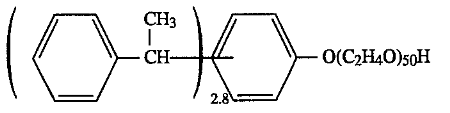

Organic diluents which may be present in the spray mixtures which can be used according to the invention are all polar and non-polar organic solvents which can conventionally be used for such purposes. The following are preferably suitable: ketones, such as methyl isobutyl ketone and cyclohexanone, furthermore amides, such as dimethylformamide, moreover cyclic compounds, such as N-methyl-pyrrolidone, N-octyl-pyrrolidone, N-dodecyl-pyrrolidone, N-octyl-caprolactam, N-dodecylcaprolactam and γ-butyrolactone, additionally strongly polar solvents, such as dimethyl sulphoxide, furthermore aromatic hydrocarbons, such as xylene, and also esters, such as propylene glycol monomethyl ether acetate, dibutyl adipate, hexyl acetate, heptyl acetate, tri-n-butyl citrate and di-n-butyl phthalate, and furthermore alcohols, such as ethanol, n- and i-propanol, n-and i-butanol, n- and i-amyl alcohol, benzyl alcohol and 1-methoxy-2-propanol.

Acids which may be present in the spray mixtures which can be used according to the invention are all inorganic and organic acids which can conventionally be employed for such purposes. The following are preferably suitable: aliphatic and aromatic hydroxycarboxylic acids, such as citric acid, salicylic acid and ascorbic acid.

Low-temperature stabilizers which may be present in the spray mixtures which can be used according to the invention are all substances which are conventionally possible for this purpose. The following are preferably suitable: urea, glycerin and propylene glycol.

Adhesives which can be employed in the spray mixtures which can be used according to the invention are all substances which are conventionally possible for this purpose. The following are preferably suitable: adhesives such as carboxymethylcellulose, natural and synthetic polymers in the form of powders, granules or latices, such as gum arabic, polyvinyl alcohol, polyvinyl acetate, and also natural phospholipids, such as cephalins and lecithins, and synthetic phospholipids. Other additives can be mineral or vegetable oils.

In addition to the phosphoric esters of the formula (I), further crystallization inhibitors can be contained in the spray mixtures which can be used according to the invention. A mixture is suitable here which consists on average of 5% of N-N-dimethylhexanamide, 50% of N,N-dimethyloctanamide, 40% of N,N-dimethyldecanamide and 5% of N,N-dimethyldodecanamide.

Besides, the spray mixtures which can be used according to the invention in each case contain water.

The concentration of active compound in the spray mixtures which can be used according to the invention can be varied within a certain range. In general, the concentrations of active compound are between 0.0003 and 5 per cent by weight, preferably between 0.003 and 3 per cent by weight.

The ratio of active compound of the formulae (II) to (VI) to phosphoric ester of the formula (I) can also be varied within a certain range. In general, the weight ratio of active compound from group (A) to phosphoric ester of the formula (I) is between 1:0.2 and 1:5, preferably between 1:0.6 and 1:2.

The amounts of other active compounds or additives in the spray mixtures which can be used according to the invention can be varied within a substantial range. They are in the order of magnitude conventionally found in such aqueous spray mixtures.

The spray mixtures which can be used according to the invention are prepared by conventional methods. In general, a procedure is followed in which a concentrate is first prepared by combining the components required in any desired sequence at temperatures between 10° C. and 30° C., mixing the batch until homogeneous, and, if appropriate, filtering the resulting mixture. To prepare the spray mixtures ready for use, the concentrated formulation is mixed with the quantity of water desired in each case, if appropriate with stirring and/or pumping, so as to distribute the formulation in the water in a uniform and finely dispersed manner.

All mixing apparatus and spray equipment conventionally suitable for these purposes can be employed for the preparation of the concentrated formulations and for the preparation and application of the spray mixtures which can be used according to the invention.

By using phosphoric esters of the formula (I) in aqueous spray mixtures based on active compounds of the formulae (II) to (VI), the crystallization of active compound both in the concentrated, commercially available formulation and during application of the aqueous spray mixtures made with this formulation in the filters and outlet openings of the spray equipment is either prevented completely or inhibited to such an extent that application of the spray mixtures is not adversely affected.

The preparation and the crystallization behaviour of the spray mixtures which can be used according to the invention are illustrated by the examples which follow.

PREPARATION EXAMPLES

EXAMPLE 1

To prepare a formulation, 25.0 parts by weight of 1-(4-chlorophenyl)-4,4-dimethyl-3-(1,2,4-triazol-1-yl-methyl)-pentan-3-ol of the formula

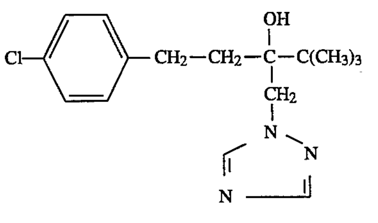

(II-a)

40.0 parts by weight of tri-n-butyl phosphate 6.5 parts by weight of (2-hydroxyethyl)-ammonium 4-(n-dodecyl)-benzene-sulphonate, 6.5 parts by weight of emulsifier of the average composition of the formula

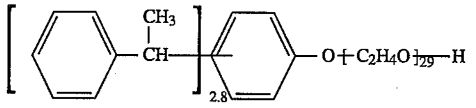

20.0 parts by weight of N-methyl-pyrrolidone and 2.0 parts by weight of water are mixed at room temperature and stirred to give a homogeneous liquid. With the resulting concentrate, a spray mixture which contains the concentrate at a concentration of 0.5% by weight is prepared by mixing it with water of a defined hardness (CIPAC-C water).

CIPAC-C water=water which contains 4 mmol of calcium chloride and 1 mmol of magnesium chloride per liter.

EXAMPLE 2

To prepare a formulation, 25.0 parts by weight of 1-(4-chlorophenyl)-4,4-dimethyl- 3-(1,2,4-triazol-1-yl-methyl)-pentan-3-ol of the formula

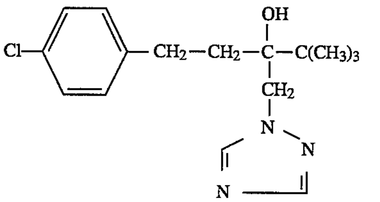

(II-a)

20.0 parts by weight of tri-n-butyl phosphate, 6.5 parts by weight of (2-hydroxyethyl)-ammonium 4-(n-dodecyl)-benzene-sulphonate, 6.5 parts by weight of the emulsifier of the average composition of the formula

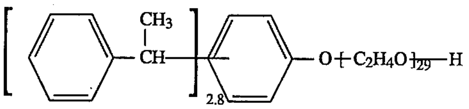

5.0 parts by weight of N-methyl-pyrrolidone 2.0 parts by weight of water 35.0 parts by weight of a mixture of, on average,
- 5% of N,N-dimethylhexanamide,
- 50% of N,N-dimethyloctanamide,
- 40% of N,N-dimethyldecanamide and
- 5% of N,N-dimethyldodecanamide, are mixed at room temperature and stirred to give a homogeneous liquid. With the resulting concentrate, a spray mixture which contains the concentrate at a concentration of 0.5% by weight is prepared by mixing it with water of a defined hardness (CIPAC-C water; cf. Example 1).

EXAMPLE 3

To prepare a formulation, 25.0 parts by weight of 1-(4-chlorophenyl)-4,4-dimethyl-3-( 1,2,4-triazol-1-yl)-methyl)-penta-3-ol of the formula

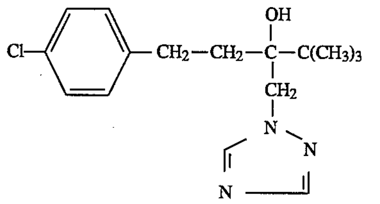

(II-a)

20.0 parts by weight of tri-n-butyl phosphate, 35.0 parts by weight of a mixture of, on average,
- 5% of N,N-dimethylhexanamide,
- 50% of N,N-dimethyloctanamide,
- 40% of N,N-dimethyldecanamide and
- 5% of N,N-dimethyldodecanamide and 20.0 parts by weight of a reaction product of castor oil with ethylene oxide in the molar ratio 1:30 are mixed at room temperature and stirred to give a homogeneous liquid. With the resulting concentrate, a spray mixture which contains the concentrate at a concentration of 0.5% by weight is prepared by mixing it with water of a defined hardness (CIPAC-C water, cf. Example 1).

EXAMPLE 4

To prepare a formulation, 25.0 parts by weight of 1-(4-chlorophenyl)-4,4-dimethyl-3-(1,2,4-triazol-1-yl)-methyl)-pentan-3-ol of the formula

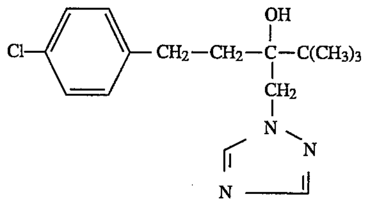

(II-a)

20.0 parts by weight of tri-(2-ethyl-hexyl)phosphate, 35.0 parts by weight of a mixture of, on average,
- 5% of N,N-dimethylhexanamide,
- 50% of N,N-dimethyloctanamide,
- 40% of N,N-dimethyldecanamide and
- 5% of N,N-dimethyldodecanamide 6.5 parts by weight of the emulsifier of the average composition of the formula

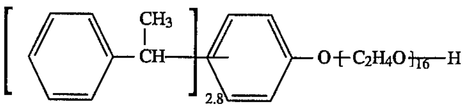

6.5 parts by weight of 4-(n-dodecyl)-benzene-sulfonic acid (2-hydroxyethyl)ammonium salt, 5.0 parts by weight of N-methylpyrrolidone and 2.0 parts by weight of water are mixed at room temperature and stirred to give a homogeneous liquid. With the resulting concentrate, a spray mixture which contains the concentrate at a concentration of 0.5% by weight is prepared by mixing it with water of a defined hardness (CIPAC-C water, cf. Example 1).

EXAMPLE 5

To prepare a formulation, 25.0 parts by weight of 1-(4-chlorophenyl)-4,4-dimethyl-3-(1,2,4-triazol-1-yl)-methyl)-pentan-3ol of the formula

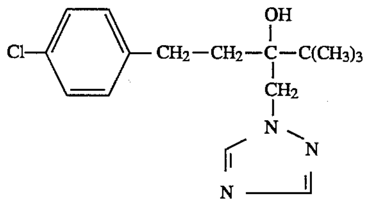

(II-a)

30.0 parts by weight of tri-n-butyl phosphate, 20.0 parts by weight of N-octylcaprolactam, 9.0 parts by weight of N-methylpyrrolidone, 8.0 parts by weight of the emulsifier of the average composition of the formula

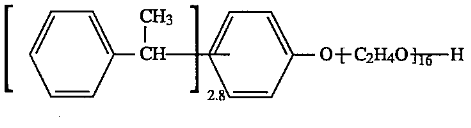

and 8.0 parts by weight of 4-(n-dodecyl)-benzene-sulfonic acid (2-hydroxyethyl)ammonium salt, are mixed at room temperature and stirred to give homogeneous liquid. With the resulting concentrate, spray mixture which contains the concentrate at concentration of 0.5% by weight is prepared by mixing it with water of a defined hardness (CIPAC-C water, cf. Example 1).

Example A (Comparison)

Known from EP-OS (European Published Specification) 0 453 899

To prepare a formulation 25.0 parts by weight of 1-(-4-chlorophenyl)-4,4-dimethyl-3-(1,2,4-triazol-1-yl-methyl)-pentan-3-ol of the formula

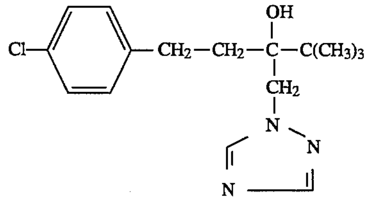

(II-a)

35.0 parts by weight of a mixture of, on average,
5% of N,N-dimethylhexanamide,
50% of N,N-dimethyloctanamide,
40% of N,N-dimethyldecanamide and
5% of N,N-dimethyldodecanamide, 6.5 parts by weight of the emulsifier of the average composition of the formula

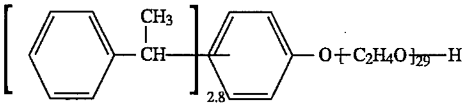

20.0 parts by weight of N-octyl-pyrrolidone, 5.0 parts by weight of N-methyl-pyrrolidone, 6.5 parts by weight of (2-hydroxyethyl)-ammonium 4-(n-dodecyl)-benzene-sulphonate and 2.0 parts by weight of water are mixed at room temperature and stirred to give a homogeneous liquid. With the resulting concentrate, a spray mixture which contains the concentrate at a concentration of 0.5% by weight is prepared by mixing it with water of a defined hardness (CIPAC-C water; cf. Example 1).

Use Example

To test the crystallization properties, in each case 250 ml of an aqueous spray mixture with a concentrate content of 0.5% by weight are constantly recirculated by pumping the mixture through a fine-meshed sieve in a flow apparatus at a temperature of 5° C. The crystal deposition on the sieve is determined indirectly by measuring the differential pressure on the sieve. A great increase in pressure shows that the meshes of the sieve are clogged to a large extent by crystal deposition.

The formulations employed and the test results can be seen from the table which follows.

TABLE 1

| Formulation of Example | Crystal deposition on the sieve of the flow apparatus |
|---|---|
| 1 (According to the invention) | After 9.9 hours start of crystal deposition on the sieve |
| 2 (According to the invention) | After 8.5 hours start of crystal deposition on the sieve |
| 3 (According to the invention) | After 11.8 hours start of crystal deposition on the sieve |
| 4 (According to the invention) | After 9.4 hours start of crystal deposition on the sieve |
| 5 (According to the invention) | After 100 hours still no crystal deposition on the sieve |
| A (Known) | After 6.4 hours start of crystal deposition on the sieve |

It is understood that the specification and examples are illustrative but not limitative of the present invention and that other embodiments within the spirit and scope of the invention will suggest themselves to those skilled in the art.

We claim:

1. Process for preventing the crystallization of spray mixtures comprising

A) at least one azole derivative of the formula

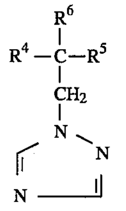

in which a) $R^4$ represents

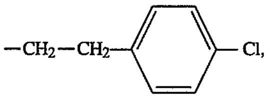

$R^5$ represents tert-butyl and $R^6$ represents hydroxyl, or b) $R^4$ represents 4-fluorophenyl, $R^5$ represents 2-fluorophenyl and $R^6$ represents hydroxyl, or c) $R^4$ represents 2,4-dichlorophenyl, $R^5$ represents n-butyl and $R^6$ represents hydroxyl, or d) $R^4$ represents

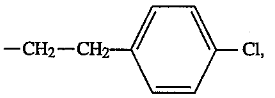

$R^5$ represents phenyl and $R^6$ represents cyano, or e) $R^4$ represents 4-chlorophenyl, $R^5$ represents

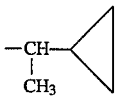

and $R^6$ represents hydroxyl, and/or at least one azole derivative of the formula

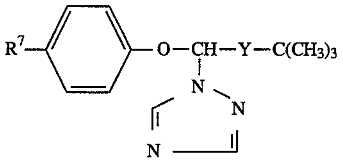

in which a) Y represents —CH(OH) and $R^7$ represents chlorine or phenyl, or b) Y represents CO and $R^7$ represents chlorine, and/or at least one azole derivative of the formula

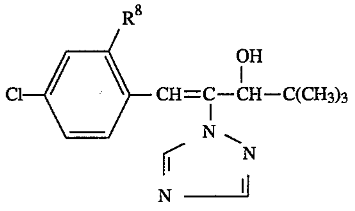

in which $R^8$ represents hydrogen or chlorine, and/or 1-([bis -(4-fluorophenyl)-methyl-silyl]-methyl)-1H-( 1,2,4-triazole) of the formula

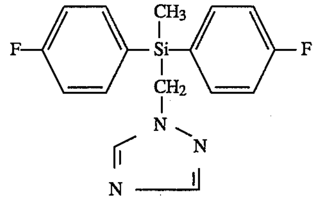

and/or

1-[3-(2-chlorophenyl)-2-(4-fluorophenyl)-oxiran-2-yl-methyl]-1H-(1,2,4-triazole) of the formula

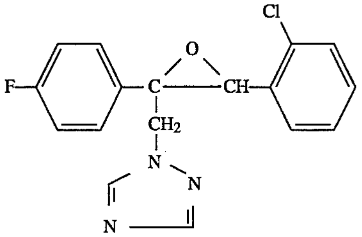

and

B) if appropriate one or more other active compounds and additives, upon spraying said mixtures, which process is characterized in that at least one phosphoric ester of the formula

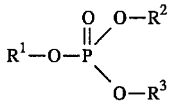

in which $R^1$ represents alkyl having 2 to 18 carbon atoms and $R^2$ and $R^3$ independently of one another represent alkyl having 2 to 12 carbon atoms, is added to the spray mixtures.

2. Process according to claim 1, characterized in that a phosphoric ester is employed in which $R^1$ represents straight-chain or branched alkyl having 4 to 12 carbon atoms, $R^2$ represents straight-chain or branched alkyl having 2 to 8 carbon atoms and $R^3$ represents straight-chain or branched alkyl having 2 to 8 carbon atoms.

3. Process according to claim 1, characterized in that a phosphoric ester is employed in which $R^1$ represents n-butyl, iso-butyl, sec-butyl, tert-butyl, n-pentyl, n-hexyl, 2-ethyl-hexyl, n-heptyl, n-octyl, iso-octyl, n-nonyl, iso-nonyl, n-decyl, n-dodecyl or iso-dodecyl, $R^2$ represents ethyl, n-butyl, iso-butyl, sec-butyl, tert-butyl, n-pentyl, n-hexyl, 2-ethyl-hexyl, n-heptyl, n-octyl or iso-octyl, and $R^3$ represents ethyl, n-butyl, iso-butyl, sec-butyl, tert-butyl, n-pentyl, n-hexyl, 2-ethyl-hexyl, n-heptyl, n-octyl or iso-octyl.

4. Process according to claim 1, characterized in that the phosphoric ester employed is tri-n-butyl phosphate.

5. Process according to claim 1, characterized in that the phosphoric ester employed is tri-n-butyl phosphate and the compound of Group (A) is 1-(4-chlorophenyl)- 4,4-dimethyl-3-(1,2,4-triazol-1-yl)-methyl)-pentan-3-ol of the formula

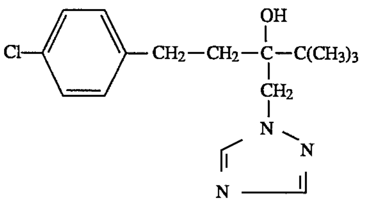

6. Process according to claim 1, wherein the phosphoric ester is present in about 0.2 to 5 times the weight of azole derivative (A).

7. A composition comprising

A) at least one azole derivative of the formula

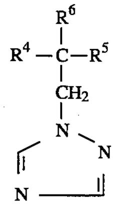

in which a) $R^4$ represents

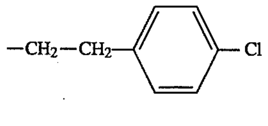

$R^5$ represents tert-butyl and
$R^6$ represents hydroxyl, or b) $R^4$ represents 4-fluorophenyl, $R^5$ represents 2-fluorophenyl and $R^6$ represents hydroxyl, or c) $R^4$ represents 2,4-dichlorophenyl, $R^5$ represents n-butyl and $R^6$ represents hydroxyl, or d) $R^4$ represents

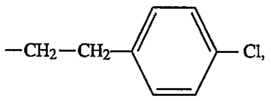

$R^5$ represents phenyl and $R^6$ represents cyano, or e) $R^4$ represents 4-chlorophenyl, $R^5$ represents

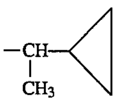

and $R^6$ represents hydroxyl, or at least one azole derivative of the formula

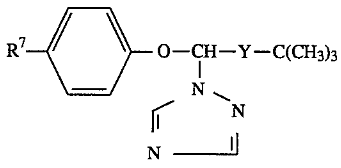

in which a) Y represents —CH(OH) and $R^7$ represents chlorine or phenyl, or b) Y represents CO and $R^7$ represents chlorine, or at least one azole derivative of the formula

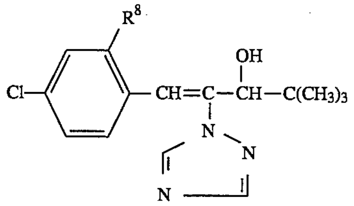

in which $R^8$ represents hydrogen or chlorine, or 1-([bis-(4-fluorophenyl)-methyl-silyl]-methyl)-1H-(1,2,4-triazole) of the formula

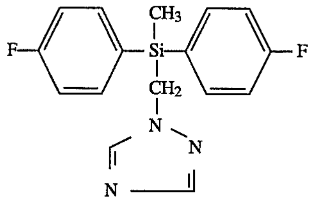

or
1-[3-(2-chlorophenyl)-2-(4-fluorophenyl)-oxiran-2-yl-methyl]-1H-(1,2,4-triazole) of the formula
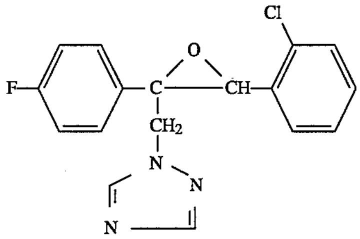
and (B) at least one phosphoric ester of the formula
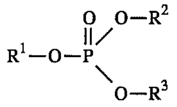
in which
$R^1$ represents alkyl having 2 to 18 carbon atoms and
$R^2$ and $R^3$ independently of one another represent alkyl having 2 to 12 carbon atoms,
which composition does not crystallize when sprayed as an aqueous solution or emulsion.
* * * * *

UNITED STATES PATENT AND TRADEMARK OFFICE

CERTIFICATE OF CORRECTION

PATENT NO. : 5,476,845

DATED : December 19, 1995

INVENTOR(S) : Reizlein, et al.

It is certified that error appears in the above-indentified patent and that said Letters Patent is hereby corrected as shown below:

Title Page Insert -- OTHER DOCUMENTS: English Abstract of JP 6157202 (7/7/92) --

Signed and Sealed this

Twenty-seventh Day of August, 1996

Attest:

Bruce Lehman

BRUCE LEHMAN

*Attesting Officer* *Commissioner of Patents and Trademarks*